United States Patent
Saraganachari et al.

(10) Patent No.: US 10,722,498 B2
(45) Date of Patent: Jul. 28, 2020

(54) ACETAZOLAMIDE OPHTHALMIC SOLUTION

(71) Applicants: INNOVATIVE NANO & MICRO TECHNOLOGIES PVT LTD (INM TECHNOLOGIES), Bangalore (IN); SHILPA MEDICARE LIMITED, Karnataka (IN)

(72) Inventors: Andanayya Saraganachari, Bangalore (IN); Abhilash Narayanaswamy, Bangalore (IN); Sreenivasa Reddy, Bangalore (IN); Shivakumar Pradeep, Vizianagaram (IN)

(73) Assignee: SHILPA MEDICARE LIMITED, Raichur, Karnataka ( * ) Notice: Subject to any disclaimer, the term of this patent is extended or adjusted under 35 U.S.C. 154(b) by 0 days.

(21) Appl. No.: 16/344,803

(22) PCT Filed: Jan. 22, 2018

(86) PCT No.: PCT/IB2018/050371
§ 371 (c)(1),
(2) Date: Apr. 25, 2019

(87) PCT Pub. No.: WO2018/138621
PCT Pub. Date: Aug. 2, 2018

(65) Prior Publication Data
US 2020/0054612 A1    Feb. 20, 2020

(30) Foreign Application Priority Data
Jan. 27, 2017  (IN) .............................. 201741003106

(51) Int. Cl.
*A61K 31/433*    (2006.01)
*A61P 27/02*    (2006.01)
*A61K 47/32*    (2006.01)
*A61K 47/40*    (2006.01)

(52) U.S. Cl.
CPC ............ *A61K 31/433* (2013.01); *A61K 47/32* (2013.01); *A61K 47/40* (2013.01); *A61P 27/02* (2018.01)

(58) Field of Classification Search
CPC ............................. A61K 31/433; A61P 27/02
USPC ......................................................... 514/363
See application file for complete search history.

(56) References Cited

U.S. PATENT DOCUMENTS 5,324,718 A    6/1994    Loftsson

FOREIGN PATENT DOCUMENTS

WO    2001089578 A1    11/2001

OTHER PUBLICATIONS

Zhu et al., "The development of polycarbophil as a bioadhesive material in pharmacy", Asian Journal of Pharmaceutical Sciences, vol. 8, No. 4, pp. 218-227 (2013).*
The Englsih translation for WO 01/89578 A1 (2001) of PTO-1449.*

* cited by examiner

*Primary Examiner* — Kevin E Weddington

(57) ABSTRACT

The present invention provides a stable, ophthalmic aqueous composition for topical administration comprising acetazolamide and an aqueous liquid capable of forming a pharmaceutically acceptable gel in situ when applied topically to a patient, said composition has the pH of less than 4.5.

5 Claims, No Drawings

ACETAZOLAMIDE OPHTHALMIC SOLUTION

FIELD OF INVENTION

The present invention relates to eye drops for the treatment of glaucoma. It relates more specifically an eye drop containing acetazolamide.

BACKGROUND OF THE INVENTION

Acetazolamide is a carbonic anhydrase inhibitor, an ocular hypotensive agent when it is administered systemically; it is widely used for the treatment of glaucoma. Acetazolamide has very low solubility in water.

U.S. Pat. No. 5,324,718 discloses the eye drop preparations comprising acetazolamide, hydroxypropyl-β-cyclodextrin in presence of a water soluble polymer such as hydroxypropyl cellulose.

PCT Patent Publication No. WO2001089578A1 discloses the eye drop preparations comprising acetazolamide, hydroxypropyl-β-cyclodextrin, a water soluble stabilizing polymer which further comprises a polymer selected from a hydroxyethylcellulose and methyl cellulose.

Eye drops as disclosed in above prior art does not provide the sufficient duration of action and/or efficacy.

The present invention aims to provide acetazolamide eye drops with extended duration of action and/or efficacy.

SUMMARY OF THE INVENTION

In one object, the present invention provides an aqueous ophthalmic composition comprising acetazolamide, cyclodextrin, water soluble polymer, a high molecular weight acrylic acid polymer crosslinked with divinyl glycol-containing polymer and water.

In another object, the present invention provides an aqueous ophthalmic composition consisting essentially of acetazolamide, high molecular weight acrylic acid polymer crosslinked with divinyl glycol-containing polymer and water.

In yet another object, the present invention provides an aqueous ophthalmic composition consisting of acetazolamide, hydroxypropyl-β-cyclodextrin, polyvinyl alcohol, polycarbophil and water.

DETAILED DESCRIPTION OF THE INVENTION

The present invention provides an aqueous ophthalmic composition comprising acetazolamide, cyclodextrin, water soluble polymer, a high molecular weight acrylic acid polymer crosslinked with divinyl glycol-containing polymer and water.

An aqueous ophthalmic composition can be an aqueous solution, aqueous suspension or aqueous gel.

A high molecular weight acrylic acid polymer crosslinked with divinyl glycol-containing polymer used in the present invention prolong the retention time of the acetazolamide at the surface of the eye. The extended period of action is obtained by the in-situ gelling properties of the high molecular weight acrylic acid polymer crosslinked with divinyl glycol-containing polymer in the physiological pH of the eye and further the bioadhesive properties of the high molecular weight acrylic acid polymer crosslinked with divinyl glycol-containing polymer. In one preferred embodiment the high molecular weight acrylic acid polymer crosslinked with divinyl glycol-containing polymer used in the present invention is polycarbophil such as NOVEON AA-1. Preferably high molecular weight acrylic acid polymer crosslinked with divinyl glycol-containing polymer is in an amount of about 0.01 to about 2% based on the weight of the composition. The most preferred high molecular weight acrylic acid polymer crosslinked with divinyl glycol-containing polymer is in an amount of about 0.5% to about 1.5% based on the weight of the composition.

The cyclodextrin which is used in the present invention may be one of the known cyclodextrin which is used as the solubilizer or complexing agent. Particularly preferred cyclodextrin is hydroxypropyl-β-cyclodextrin. The hydroxypropyl-β-cyclodextrin is preferably used in a weight ratio of about 10:1 to about 40:1. The hydroxypropyl-β-cyclodextrin is more preferably used in a weight ratio of 20:1 to acetazolamide.

In the present invention the aqueous ophthalmic composition comprises the concentrations with an amount of about 0.2% to about 2% by weight of acetazolamide. The most preferred concentrations are 0.5% and 1% by weight of acetazolamide.

Water soluble polymer, when combined with cyclodextrin, allows the maintenance of solubility of acetazolamide especially at its optimum pH stability with various polymers. The preferred water soluble polymer in the present invention is polyvinyl alcohol. Polyvinyl alcohol is present in the concentration of about 0.1% to about 1% by weight of the composition. Most preferred concentration of polyvinyl alcohol in the composition is about 0.1% to about 0.5% by weight.

In accordance with this invention, the pH is adjusted below 5 in order to secure a useful shelf life. The maximum stability of the ophthalmic solution of acetazolamide is achieved when the pH is maintained at a pH of 4.5 or below. The pH of the solution is adjusted with the Hydrochloric acid or sodium hydroxide.

In further embodiments of the invention, the aqueous ophthalmic composition of the present invention comprises other inactive ingredients such as chelating agents, preservatives, antioxidants and isotonizing agents.

The chelating agent in the present aqueous ophthalmic composition is preferably at least one type selected from the group consisting of edetic acid, citric acid, metaphosphoric acid, pyrophosphoric acid, polyphosphoric acid, malic acid, tartaric acid, phytic acid, and salts thereof; more preferably at least one type selected from the group consisting of edetic acid, citric acid, metaphosphoric acid, polyphosphoric acid, and salts thereof; and particularly preferably a salt of edetic acid, i.e disodium EDTA. In the present aqueous ophthalmic composition, the chelating agent is preferably at a concentration of 0.001 to 1% by weight in the ophthalmic composition. Most preferably the chelating agent is used in the concentration of about 0.5% by weight of the ophthalmic composition.

The isotonizing agents present in the present aqueous ophthalmic composition are preferably at least one type selected form the group consisting of sodium chloride, potassium chloride, and concentrated glycerin. In the present aqueous ophthalmic composition, the preferable isotonizing agent used is sodium chloride. The isotonizing agent is preferable used at a concentration of 0.001 to 1% by weight in the ophthalmic composition. Most preferably the isotonizing agent is used in the concentration of about 0.2% by weight of the ophthalmic composition.

In the embodiments of the present invention, aqueous ophthalmic composition comprises a preservative. The preservatives are selected from group consisting of benzalkonium chloride (BAK), sorbic acid, chlorobutanol, disodium ethylenediamine tetra-acetate, polyquarternium-1 or alkyltrimethylammonium bromide. Preferred preservative is benzalkonium chloride (BAK).

In the embodiments of the present invention, aqueous ophthalmic composition comprises an antioxidant. The antioxidants are selected from group consisting trisodium citrate dihydrate, ascorbyl palmitate and vitamin E acetate.

In further embodiments, the present invention provides an aqueous ophthalmic composition which is an aqueous solution consisting essentially of acetazolamide, high molecular weight acrylic acid polymer crosslinked with divinyl glycol-containing polymer and water.

In another embodiment, the present invention provides an ophthalmic composition which is an aqueous solution consisting of acetazolamide, hydroxypropyl-β-cyclodextrin, polyvinyl alcohol, polycarbophil and water.

In further embodiment, the present invention provides an ophthalmic composition which is an aqueous solution consisting of acetazolamide, hydroxypropyl-β-cyclodextrin, polyvinyl alcohol, polycarbophil and water with a pH of 4.0, when administered into eye forms the gel.

The present invention also relates to a method of increasing the time of action of an ophthalmic composition which is an aqueous solution comprising acetazolamide, cyclodextrin, water soluble polymer, a high molecular weight acrylic acid polymer crosslinked with divinyl glycol—containing polymer and water.

In embodiments of the present invention, the present invention provides an ophthalmic composition, comprising, 0.5% of acetazolamide, 10% of Hydroxypropyl-β-cyclodextrin, 0.5% of polyvinyl alcohol, 0.5% to about 1.5% of polycarbophil and water.

The following examples are provided to illustrate the present invention. It is understood, however, that the invention is not limited to the specific conditions or details described in the examples below. The examples should not be construed as limiting the invention as the examples merely provide specific methodology useful in the understanding and practice of the invention and its various aspects. While certain preferred and alternative embodiments of the invention have been set forth for purposes of disclosing the invention, modification to the disclosed embodiments can occur to those who are skilled in the art.

Examples 1 to 9

Eye drops with the following compositions are prepared.

These eye drops are prepared as follows:

In purified water, hydroxypropyl-β-cyclodextrin, polyvinyl alcohol, and acetazolamide are successively dissolved to form a homogenous solution of acetazolamide. Polycarbophil, disodium EDTA, sodium chloride, and optionally benzalkonium chloride concentrated solution was prepared separately and incorporated into the above homogenous solution of acetazolamide, pH was adjusted with hydrochloric acid to 4.5, and the final weight is adjusted if necessary with required quantity of purified water.

The viscosity was measured with an apparatus Rheometer. The operating conditions for the measurement of viscosity are at the shear rate of 1/s at the temperature 25° C.

Example 10: Measurement of Intraocular Pressure in Rabbit Eyes

The inhibition of the ocular hypertension was determined by the following protocol: The experiments were performed in new New Zealand white rabbit eyes by using tonometry method. Rabbits were divided into groups; where each group consists of 4 animals. Group 1, Group 2, Group 3, Group 4 and Group 5 of Rabbits are administered with the predetermined concentrations of ophthalmic compositions of Example 1, 2, 3, 4 and 5 respectively. Group 6 of Rabbits are administered with oral acetazolamide 12.92 mg/kg. The intraocular pressure was measured at 0, 0.5, 1, 4, 8, 12 hrs. After 6 hours, one more administration of ophthalmic composition of Example 1 was instilled in Group 1 of Rabbits and the intraocular pressure was measured.

The percentage change in the intraocular pressure is depicted in the following table 1.

TABLE 1

| Group | Time (hrs) | | | | | |
|---|---|---|---|---|---|---|
| | 0.5 | 1 | 4 | 6 | 8 | 12 |
| Group 1 (Example 1) | 4.50 | 10.60 | 12.60 | 8.50 | 12.60 | 16.70 |
| Group 2 (Example 2) | 6.30 | 18.00 | 16.00 | 21.90 | 12.10 | 10.20 |
| Group 3 (Example 3) | 9.60 | 7.70 | 13.50 | 3.80 | 0.0 | -7.7 |
| Group 4 (Example 4) | 13.33 | 7.78 | 6.67 | -2.22 | -3.33 | -8.89 |
| Group 5 (Example 5) | 10.91 | 7.27 | -10.91 | -8.18 | -7.27 | -10 |
| Group 6 (Oral acetazolamide) | 18.00 | 14.00 | 14.00 | 14.00 | 6.00 | 6.00 |

From the results it is shown that the ophthalmic composition of Example 2, Example 4 and Example 5; with the

| Ingredients | Ex: 1 | Ex: 2 | Ex: 3 | Ex: 4 | Ex: 5 | Ex: 6 | Ex: 7 | Ex: 8 | Ex: 9 |
|---|---|---|---|---|---|---|---|---|---|
| Acetazolamide | 0.5% | 0.5% | 1.0% | 0.5% | 0.5% | 0.5% | 0.5% | 1.0% | 0.5% |
| Hydroxypropyl-β-cyclodextrin. | 10% | 10% | 10% | 10% | 10% | 10% | 10% | 10% | 10% |
| Polycarbophil | 0.01% | 1.5% | 0.01% | 0.9% | 0.9% | 0.01% | 1.5% | 0.01% | 1.5% |
| Polyvinyl alcohol | 0.5% | 0.5% | 0.5% | 0.5% | 0.5% | 0.5% | 0.5% | 0.5% | 0.1% |
| Disodium EDTA | 0.5% | 0.5% | 0.5% | 0.5% | 0.5% | 0.5% | 0.5% | 0.5% | 0.5% |
| Sodium chloride | 0.2% | 0.2% | 0.2% | 0.35% | 0.35% | 0.35% | 0.35% | 0.35% | 0.35% |
| Hydrochloric acid/ Sodium hydroxide | Qs to pH 4.5 | Qs to pH 4.5 | Qs to pH 4.5 | Qs to pH 4.5 | Qs to pH 4.5 | Qs to pH 4.5 | Qs to pH 4.0 | Qs to pH 4.5 | Qs to pH 4.0 |
| Benzalkonium Chloride | — | — | — | — | 0.01% | — | — | — | — |
| Purified Water | QS | QS | QS | QS | QS | QS | QS | QS | QS | polycarbophil of about 0.5% to about 1.5% respectively has increased action with potentially reduced base line of intraocular pressure, when compared to the other ophthalmic compositions of acetazolamide with 0.01% polycarbophil and Oral acetazolamide.

Example 11: Measurement of Viscosities of Different Ophthalmic Compositions with Different pH Conditions of the Ophthalmic Composition of Example 2

The ophthalmic composition as disclosed in example 2 is adjusted with different pH such as 4.0, 4.25, 4.5, 4.75 & 5.0 using hydrochloric acid/sodium hydroxide. The viscosity of the ophthalmic composition at different compositions is measured with an apparatus Rheometer. The operating conditions for the measurement of viscosity are at the shear rate of 1/s at the temperature 25° C.

The viscosities of the ophthalmic compositions with different pH are as disclosed in Table 2.

TABLE 2

| Composition of example 2 with different pH | Viscosity (m · Pas) |
|---|---|
| 4.0 | 3370.9 |
| 4.25 | 6155.5 |
| 4.5 | 14587 |
| 4.75 | 28817 |
| 5.0 | 46411 |

From the results of viscosities, as the pH of the formulations increased, the viscosity of formulations increased. At the acidic pH the ophthalmic composition exists as the solution and on increase in pH the ophthalmic composition forms the gel. When the ophthalmic composition at the pH of 4 in the solution form is administered into the eye, it undergoes to the formation of gel at the physiological pH of eye.

The invention claimed is:

1. An aqueous ophthalmic composition comprising
   (a) about 0.2% to about 2% acetazolamide based on the weight of the composition,
   (b) cyclodextrin,
   (c) water soluble polymer,
   (d) about 0.5% to about 2% of polycarbophil based on the weight of the composition, and
   (e) water.

2. The composition according to claim 1, wherein the cyclodextrin is hydroxypropyl-β-cyclodextrin.

3. The composition according to claim 1, wherein water soluble polymer is polyvinyl alcohol.

4. The composition according to claim 1, wherein the composition further comprises antioxidants, chelating agents, preservatives and isotonicity adjusting agents.

5. An aqueous ophthalmic composition consisting essentially of
   (a) about 0.2% to about 2% acetazolamide based on the weight of the composition,
   (b) hydroxypropyl-β-cyclodextrin,
   (c) about 0.1% to about 1% of polyvinyl alcohol based on the weight of the composition,
   (d) about 0.5% to about 2% of polycarbophil based on the weight of the composition,
   (e) at least one excipient selected from antioxidant, chelating agent, preservative, isotonicity adjusting agent and
   (f) water;
   wherein the pH of the composition is about 4.0 to about 5.0.

* * * * *